US012608656B2

(12) United States Patent
Macpherson et al.

(10) Patent No.: US 12,608,656 B2
(45) Date of Patent: *Apr. 21, 2026

(54) ANCESTRY PAINTING

(71) Applicant: 23andMe, Inc., Sunnyvale, CA (US)

(72) Inventors: John Michael Macpherson, Santa Ana, CA (US); Brian Thomas Naughton, Mountain View, CA (US); Joanna Louise Mountain, Menlo Park, CA (US)

(73) Assignee: 23andMe Genomics LLC, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/098,653

(22) Filed: Apr. 2, 2025

(65) Prior Publication Data

US 2025/0259107 A1     Aug. 14, 2025

Related U.S. Application Data

(63) Continuation of application No. 18/671,542, filed on May 22, 2024, now Pat. No. 12,293,268, which is a
(Continued)

(51) Int. Cl.
*G06N 20/00* (2019.01)
*G06F 3/04812* (2022.01)
(Continued)

(52) U.S. Cl.
CPC ......... *G06N 20/00* (2019.01); *G06F 3/04812* (2013.01); *G06F 3/0484* (2013.01); *G06F 11/0793* (2013.01); *G06F 16/29* (2019.01); *G06N 5/022* (2013.01); *G06N 5/04* (2013.01); *G16B 20/00* (2019.02); *G16B 20/20*

(2019.02); *G16B 20/40* (2019.02); *G16B 30/00* (2019.02); *G16B 40/00* (2019.02); *G16B 40/20* (2019.02);
(Continued)

(58) Field of Classification Search
CPC .......... G06N 20/00; G06N 5/022; G06N 5/04; G16H 10/60; G06F 16/29
See application file for complete search history.

(56) References Cited

U.S. PATENT DOCUMENTS

| | | | |
|---|---|---|---|
| 11,238,957 B2 | 2/2022 | Byrnes | |
| 2006/0142949 A1* | 6/2006 | Helt | G16B 45/00 |
| | | | 702/20 |

FOREIGN PATENT DOCUMENTS

| | | | | |
|---|---|---|---|---|
| WO | WO-2004097712 A2 * | 11/2004 | ............. | G16B 45/00 |

OTHER PUBLICATIONS

Office Action, U.S. Appl. No. 18/922,053, mailed Aug. 26, 2025.
(Continued)

*Primary Examiner* — Lisa S Landis
(74) *Attorney, Agent, or Firm* — McDonnell Boehnen Hulbert & Berghoff LLP

(57) ABSTRACT

Displaying an indication of ancestral data is disclosed. An indication that a genetic interval corresponds to a reference interval that has a likelihood of having one or more ancestral origins is received. One or more graphic display parameters are determined based at least in part on the indication. An indication of the one or more ancestral origins is visually displayed using the one or more graphic display parameters.

20 Claims, 20 Drawing Sheets
(12 of 20 Drawing Sheet(s) Filed in Color)
Specification includes a Sequence Listing.

Related U.S. Application Data continuation of application No. 18/472,019, filed on Sep. 21, 2023, now Pat. No. 12,033,046, which is a continuation of application No. 18/180,691, filed on Mar. 8, 2023, now Pat. No. 11,803,777, which is a continuation of application No. 18/058,029, filed on Nov. 22, 2022, now Pat. No. 11,625,139, which is a continuation of application No. 17/682,761, filed on Feb. 28, 2022, now Pat. No. 11,531,445, which is a continuation of application No. 16/226,116, filed on Dec. 19, 2018, now abandoned, which is a continuation of application No. 15/267,053, filed on Sep. 15, 2016, now abandoned, which is a continuation of application No. 12/381,992, filed on Mar. 18, 2009, now abandoned.

(60) Provisional application No. 61/070,310, filed on Mar. 19, 2008.

(51) Int. Cl.

| | |
|---|---|
| *G06F 3/0484* | (2022.01) |
| *G06F 11/07* | (2006.01) |
| *G06F 16/29* | (2019.01) |
| *G06N 5/022* | (2023.01) |
| *G06N 5/04* | (2023.01) |
| *G16B 20/00* | (2019.01) |
| *G16B 20/20* | (2019.01) |
| *G16B 20/40* | (2019.01) |
| *G16B 30/00* | (2019.01) |
| *G16B 40/00* | (2019.01) |
| *G16B 40/20* | (2019.01) |
| *G16B 40/30* | (2019.01) |
| *G16B 45/00* | (2019.01) |
| *G16H 10/60* | (2018.01) |

(52) U.S. Cl.
CPC ............. *G16B 40/30* (2019.02); *G16B 45/00* (2019.02); *G16H 10/60* (2018.01)

(56) References Cited

OTHER PUBLICATIONS

Browning et al., "Population Structure With Localized Haplotype Clusters", 2010, Genetics, vol. 185 No. 4, pp. 1337-1344 (Year: 2010).

He et al., "Geographical Affinities of the Hap Map Samples", 2009, PLoS One, vol. 4 No. 3, pp. 1-8 (Year: 2009).

Menelaou et al., "Genotype calling and phasing using next-generation sequencing reads and a haplotype scaffold", Oct. 23, 2012, Bioinformatics, vol. 29 No. 1, pp. 84-91 (Year: 2012).

Notice of Allowance, U.S. Appl. No. 16/844,758, mailed Nov. 18, 2025.

* cited by examiner

100

200

300

| John Doe | ⑦ |
|---|---|
| ▓ Europe 50% | |
| ▒ Asia 50% | |
| ░ Africa 0% | |
| ▤ Not Genotyped | |

400

SEQUENCE LISTING

```
Sequence total quantity: 1
SEQ ID NO: 1              moltype = DNA   length = 21
FEATURE                  Location/Qualifiers
source                   1..21
                         mol_type = other DNA
                         organism = Homo sapiens
SEQUENCE: 1
acaagtacct tgaaaaaatt t                                          21
```

Ancestry Painting

Trace the ancestry of your chromosomes, one segment at a time.

Chromosome View

▭ Solid segments indicate that both chromosomes come from the same geographic region.
See a Cambodian Woman's painting.

▭ Dual-colored segments indicate chromosomes from different geographic regions.
See an African American Man's painting.

Select a person: | African American Man | ∨ |

```
1
2
3
4
5
6
7
8
9
10
11
12
13
14
15
16
17
18
19
20
21
22
```

African American Man　　ⓘ

Most African Americans today trace a large part their ancestry to sub-Saharan Africa as a result of the slave trade. Over the generations since, both Europeans and Native Americans have Intermarried with African Americans and contributed ancestry, as seen in the ancestry painting of this man, self-identified as African American. In fact, one of this man's chromosomes appears to be fully European across the whole genome, so it is likely that one of his parents was European.

| ■ Europe 64% |
| --- |
| ▢ Africa 33% |
| ▨ Asia 4% |
| ▨ Not Genotyped |

—402

Worldwide Examples

Click on the icons in the map below to see example painting of individuals from across the globe.

Receive an Indication that
a Genetic Interval Corresponds to a
Reference Interval that has a Likelihood
of Having One or More Ancestral Origins    ~602

Determine One or More Graphic
Display Parameters Based At Least in
Part on the Indication    ~604

Use the One or More Graphic
Display Parameters to Visually Display
an Indication of the One or More
Ancestral Origins    ~606

Receive an Individual's
Genetic Data ⟶ 702

Partition Each Chromosome
into Intervals ⟶ 704

For Each Interval, Determine a
Likelihood that the Interval is
Associated with an Ancestral Origin ⟶ 706

900

| Receive Genetic Data for a<br>Plurality of Reference Populations | ~902 |

↓

| For Each Reference Population,<br>Partition Each Chromosome of Each<br>Individual into Intervals | ~904 |

↓

| Generate a Plurality of Intervals<br>Corresponding to a Synthetic Reference<br>Population | ~906 |

↓

| Compute the Rate of Occurrence<br>of Each Interval in Each Reference<br>Population | ~908 |

1000 ⬊

Rates of Occurrence for Interval j on Chromosome i

Phased Case

| Value | African (AFR) | Asian (ASN) | European (EUR) |
|---|---|---|---|
| X | 0.12 | 0.02 | 0.85 |
| Y | 0.42 | 0.92 | 0.04 |
| Z | 0.46 | 0.06 | 0.11 |

1002 ⬊

Unphased Case

| Pair Value | AFR/AFR | ASN/ASN | EUR/EUR | AFR/ASN | ASN/EUR | AFR/EUR |
|---|---|---|---|---|---|---|
| X/X | 0.0144 | 0.0004 | 0.7225 | 0.0024 | 0.017 | 0.102 |
| X/Y | 0.0504 | 0.0184 | 0.034 | 0.1104 | 0.0008 | 0.357 |
| X/Z | 0.0552 | 0.0012 | 0.0935 | 0.0072 | 0.0022 | 0.391 |
| Y/X | 0.0504 | 0.0184 | 0.034 | 0.0084 | 0.782 | 0.0048 |
| Y/Y | 0.1764 | 0.8464 | 0.0016 | 0.3864 | 0.0368 | 0.0168 |
| Y/Z | 0.1932 | 0.0552 | 0.0044 | 0.0252 | 0.1012 | 0.0184 |
| Z/X | 0.0552 | 0.0012 | 0.0935 | 0.0092 | 0.051 | 0.0132 |
| Z/Y | 0.1932 | 0.0552 | 0.0044 | 0.4232 | 0.0024 | 0.0462 |
| Z/Z | 0.2116 | 0.0036 | 0.0121 | 0.0276 | 0.0066 | 0.0506 |

1004 ⬊

Unphased Case, Combined

| Pair Value | AFR/AFR | ASN/ASN | EUR/EUR | AFR/ASN | ASN/EUR | AFR/EUR |
|---|---|---|---|---|---|---|
| X/X | 0.0144 | 0.0004 | 0.7225 | 0.0024 | 0.017 | 0.102 |
| X/Y | 0.1008 | 0.0368 | 0.068 | 0.1188 | 0.7828 | 0.3618 |
| X/Z | 0.1104 | 0.0024 | 0.187 | 0.0164 | 0.0532 | 0.4042 |
| Y/Y | 0.1764 | 0.8464 | 0.0016 | 0.3864 | 0.0368 | 0.0168 |
| Y/Z | 0.3864 | 0.1104 | 0.0088 | 0.4484 | 0.1036 | 0.0646 |
| Z/Z | 0.2116 | 0.0036 | 0.0121 | 0.0276 | 0.0066 | 0.0506 |

FIG. 10A

Rates of Occurrence for Interval j on Chromosome i

1006 ⟍

Phased Case

| Value | African (AFR) | Asian (ASN) | European (EUR) |
|-------|---------------|-------------|----------------|
| X | B5 | C5 | D5 |
| Y | B6 | C6 | D6 |
| Z | B7 | C7 | D7 |

1008 ⟍

Unphased Case

| Pair Value | AFR/AFR | ASN/ASN | EUR/EUR | AFR/ASN | ASN/EUR | AFR/EUR |
|------------|---------|---------|---------|---------|---------|---------|
| X/X | =B5*B5 | =C5*C5 | =D5*D5 | =B5*C5 | =C5*D5 | =D5*B5 |
| X/Y | =B5*B6 | =C5*C6 | =D5*D6 | =B5*C6 | =C5*D6 | =D5*B6 |
| X/Z | =B5*B7 | =C5*C7 | =D5*D7 | =B5*C7 | =C5*D7 | =D5*B7 |
| Y/X | =B6*B5 | =C6*C5 | =D6*D5 | =B6*C5 | =C6*D5 | =D6*B5 |
| Y/Y | =B6*B6 | =C6*C6 | =D6*D6 | =B6*C6 | =C6*D6 | =D6*B6 |
| Y/Z | =B6*B7 | =C6*C7 | =D6*D7 | =B6*C7 | =C6*D7 | =D6*B7 |
| Z/X | =B7*B5 | =C7*C5 | =D7*D5 | =B7*C5 | =C7*D5 | =D7*B5 |
| Z/Y | =B7*B6 | =C7*C6 | =D7*D6 | =B7*C6 | =C7*D6 | =D7*B6 |
| Z/Z | =B7*B7 | =C7*C7 | =D7*D7 | =B7*C7 | =C7*D7 | =D7*B7 |

FIG. 10B

For Each Interval, Compute the Ratio of the Largest Frequency to the Second Largest Frequency ⟋1102

If the Ratio is Above a Threshold, then Assign the Interval the Ancestral Origin(s) Associated with the Largest Frequency ⟋1104

Use a Sliding Window to Smooth Out the Assignments ⟋1106

Based on the Assignment, Select a Color for Each Interval ⟋1108

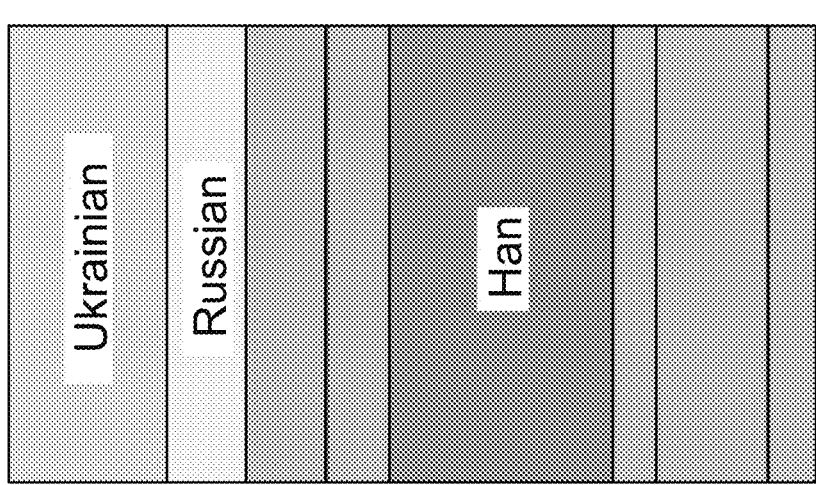
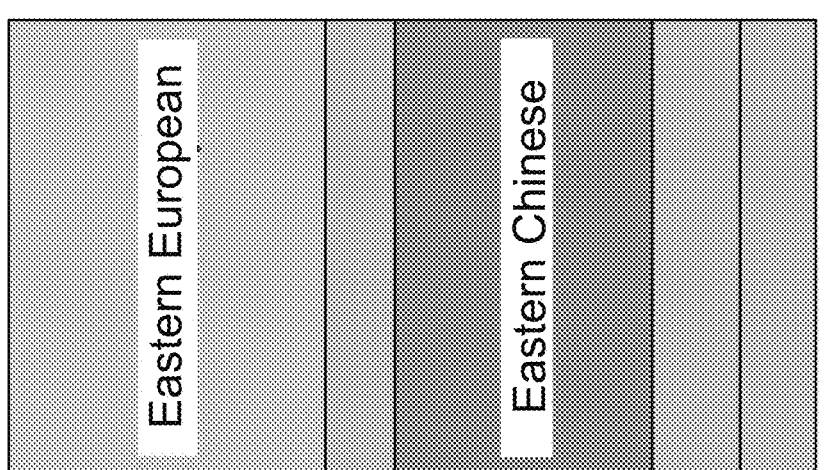
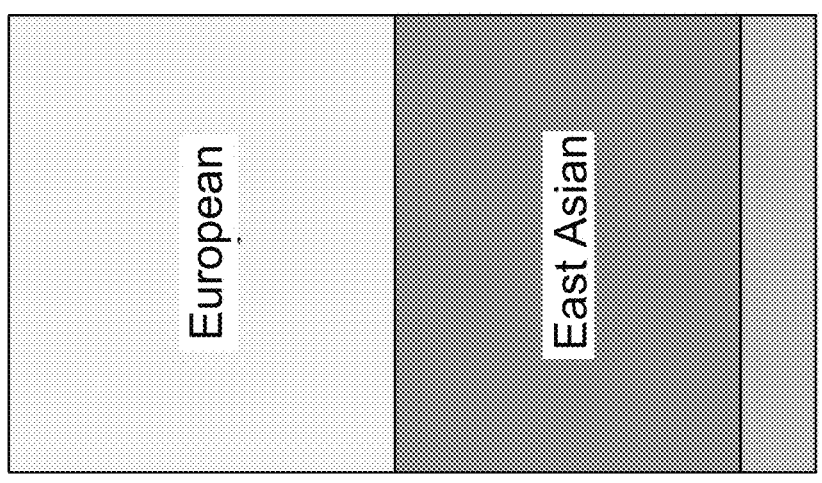
FIG. 19

ANCESTRY PAINTING

CROSS-REFERENCE TO RELATED APPLICATIONS

This application is a continuation of and claims priority to U.S. patent application Ser. No. 18/671,542, filed May 22, 2024, which is hereby incorporated by reference in its entirety.

U.S. patent application Ser. No. 18/671,542 is a continuation of and claims priority to U.S. patent application Ser. No. 18/472,019, filed Sep. 21, 2023, which is hereby incorporated by reference in its entirety.

U.S. patent application Ser. No. 18/472,019 is a continuation of and claims priority to U.S. patent application Ser. No. 18/180,691, filed Mar. 8, 2023, which is hereby incorporated by reference in its entirety.

U.S. patent application Ser. No. 18/180,691 is a continuation of and claims priority to U.S. patent application Ser. No. 18/058,029, filed Nov. 22, 2022, which is hereby incorporated by reference in its entirety.

U.S. patent application Ser. No. 18/058,029 is a continuation of and claims priority to U.S. patent application Ser. No. 17/682,761, filed Feb. 28, 2022, which is hereby incorporated by reference in its entirety.

U.S. patent application Ser. No. 17/682,761 is a continuation of and claims priority to U.S. patent application Ser. No. 16/226,116, filed Dec. 19, 2018, which is hereby incorporated by reference in its entirety.

U.S. patent application Ser. No. 16/226,116 is a continuation of and claims priority to U.S. patent application Ser. No. 15/267,053, filed Sep. 15, 2016, which is hereby incorporated by reference in its entirety.

U.S. patent application Ser. No. 15/267,053 is a continuation of and claims priority to U.S. patent application Ser. No. 12/381,992, filed Mar. 18, 2009, which is hereby incorporated by reference in its entirety.

U.S. patent application Ser. No. 12/381,992 claims priority to U.S. provisional patent application No. 61/070,310, filed Mar. 19, 2008, which is hereby incorporated by reference in its entirety.

SEQUENCE LISTING

This application contains a Sequence Listing which is submitted electronically and is hereby incorporated by reference in its entirety. The sequence listing submitted herewith is contained in the XML filed created Mar. 8, 2023 entitled "22-1253-US-CON8_Sequence-Listing.xml" and is 1,716 bytes in size.

BACKGROUND OF THE INVENTION

The instructions for making the cells in the human body are encoded in deoxyribonucleic acid (DNA). DNA is a long, ladder-shaped molecule, in which each corresponding rung is made up of a pair of interlocking units, called bases, that are designated by the four letters in the DNA alphabet—A, T, G and C. A always pairs with T, and G always pairs with C. The sequence that makes up an individual's DNA is referred to as the individual's genome.

The long molecules of DNA in cells are organized into pieces called chromosomes. Humans have 23 pairs of chromosomes. Chromosomes are further organized into short segments of DNA called genes. The different letters A, T, G, and C, which make up a gene, dictate how cells function and what traits to express by dictating what proteins the cells will make. Proteins do much of the work in the body's cells. Some proteins give cells their shape and structure. Others help cells carry out biological processes like digesting food or carrying oxygen in the blood. Using different combinations of the As, Cs, Ts and Gs, DNA creates the different proteins and regulates when and how they are turned on. Genetic or genotypic data includes information about an individual's DNA sequence, including his or her genome or particular regions of the genome. Regions of a particular individual's genome can also be referred to as DNA or genetic sequences.

Genotypic data includes single nucleotide polymorphisms (SNPs), which are the variations in the DNA sequence that occur at particular locations in an individual's DNA sequence. SNPs can generate biological variation between people by causing differences in the genetic recipes for proteins. Different variants of each SNP are called alleles. Those differences can in turn influence a variety of traits such as appearance, disease susceptibility or response to drugs. While some SNPs lead to differences in health or physical appearance, some SNPs seem to lead to no observable differences between people at all.

Unlike the sex chromosomes and the mitochondrial DNA, which are inherited as blocks, the 22 biparental chromosomes, known as autosomes, are scrambled during reproduction. Through a process known as recombination, each parent pulls his or her paired set of 22 autosomes into chunks, then reassembles a new single set using half the material from each pair. The two single sets of chromosomes from each parent are combined into a new paired set when a sperm fertilizes an egg. Every region of a person's autosomes (non-sex chromosomes) is represented by a pair of DNA sequences, one inherited from the mother and one from the father.

Scientific research today shows that the family trees of all humans living today lead back to an African homeland about 200,000 years ago. The more recent heritage of an individual's chromosomes, however, may have arisen from a population associated with a pre-colonial (before the era of intercontinental travel) home continent, such as Africa, Asia or Europe.

BRIEF DESCRIPTION OF THE DRAWINGS

The file of this patent contains at least one drawing executed in color. Copies of this patent with color drawings will be provided by the Patent and Trademark Office upon request and payment of the necessary fee.

Various embodiments of the invention are disclosed in the following detailed description and the accompanying drawings.

FIG. 4 is a diagram illustrating an embodiment of a display of ancestral data for an individual of African American descent.

FIG. 10A illustrates examples of genotype frequency tables.

For clarity, FIG. 10B illustrates how the values are obtained when going from table 1000 to table 1002.

FIG. 19 is a diagram illustrating an embodiment of a tabular view of a display of ancestral data for an individual.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Figure 1:
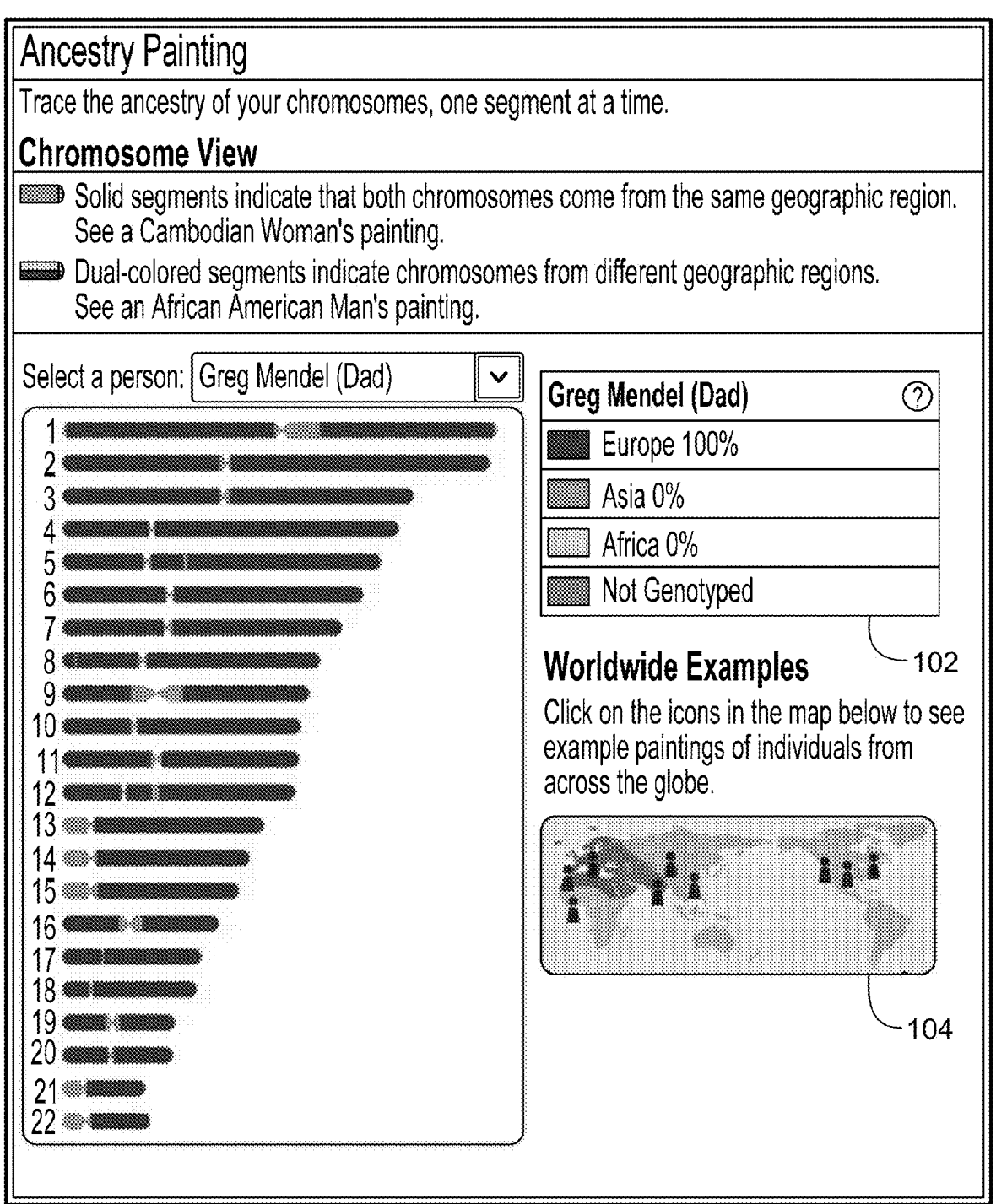
FIG. 1 is a diagram illustrating an embodiment of a display of ancestral data for an individual of European descent.

FIG. 1 is a diagram illustrating an embodiment of a display of ancestral data for an individual of European descent. Display 100 indicates ancestral origins for Greg Mendel, an example individual whose parents and grandparents are of European descent. Three of his grandparents are German and one is Norwegian.

In display 100, the 22 chromosomes are graphically displayed and each interval of each chromosome is colored according to legend 102. In this example, blue indicates European ancestral origin, orange indicates Asian ancestral origin, green indicates African ancestral origin, and gray indicates that that interval has not been genotyped. For example, a genotyping chip might have no or few markers present at those regions of the genome. Display 100 shows an example of ancestry painting, in which color is used to "paint" ancestral origins. This painting technique allows ancestral data to be conveyed to a user in a way that is easy and intuitive to understand. Although color may be described in the examples herein, in various embodiments, any other type of fill may be used, such as shading, hatching, or other patterns. In some embodiments, other visual cues besides color or fill may be used to display ancestral origins.

Although every person has two copies of each chromosome—one from the mother and one from the father—this display depicts only one set of chromosomes in order to make it easier to read. Thus, each single chromosome drawn in the painting really represents the composition of two paired chromosomes, as will be more fully illustrated below.

As shown in legend 102, Greg Mendel's 22 autosomes have 100% European ancestral origin. In some embodiments, this percentage is determined by adding up the lengths of the segments attributed to each population, as displayed, and then dividing by the total length. The numbers may be rounded to the nearest whole number. In this example, the grayed out regions are not genotyped and therefore not included in the percentage calculations.

Map 104 includes icons placed at various regions across the globe. Clicking on an icon causes the display to depict ancestral data for an example individual from the region where the icon is located. Examples of this are more fully described below.

Although the examples herein may show and describe autosomes (the non-sex chromosomes), in various embodiments, these techniques may be applied to one or more of the X chromosome, Y chromosome, mitochondrial genome, or any other appropriate genetic regions.

Figure 2:
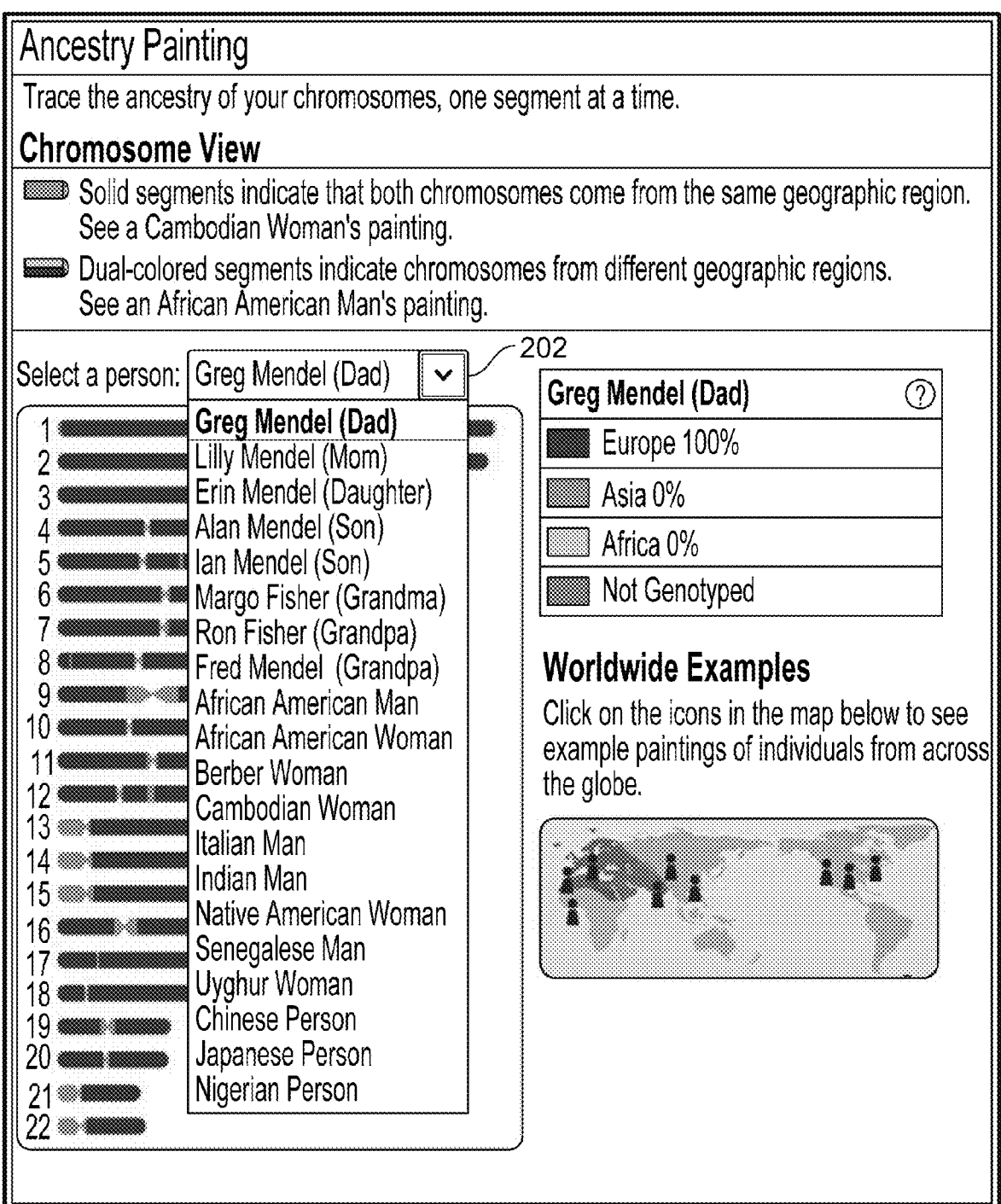
FIG. 2 is a diagram illustrating an embodiment of a display of ancestral data for an individual of European descent, including a pull-down menu.

FIG. 2 is a diagram illustrating an embodiment of a display of ancestral data for an individual of European descent, including a pull-down menu. Display 200 shows display 100 after a user has selected pull-down menu 202. Pull-down menu 202 includes a list of individuals from which to select. In some embodiments, the list includes individuals who have allowed sharing of their genetic data with the user. Some individuals in the list are not identified by name, such as "African American Man" or "Uyghur Woman." These are unidentified individuals that are provided as examples for illustrative purposes. The anonymous Italian, Cambodian, and Senegalese sample individuals have similarly uniform paintings to Greg Mendel's.

Figure 3:
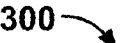
FIG. 3 is a diagram illustrating an embodiment of a display of ancestral data for an individual of Asian and European descent.

FIG. 3 is a diagram illustrating an embodiment of a display of ancestral data for an individual of Asian and European descent. Display 300 indicates ancestral origins for John Doe, an individual who has a mother of Chinese ancestry and a father of Northern European ancestry.

In display 300, each chromosome is displayed as half orange and half blue, an indication that one autosome of each pair originated in Europe and the other in Asia. Suppose John Doe had a daughter with a woman of Chinese ancestry. The child would get 22 autosomes from her mother. So one half of each chromosome in her display would be solid orange. The other half would be a roughly 50/50 mix of orange and blue bands—a reflection of her father's half-European, half-Asian ancestry.

If one were to follow the same family over the years, each new generation's ancestry paintings would grow more or less colorful depending on the continental diversity of their parents, grandparents, and so on. If no more people of non-Asian descent joined the pedigree, recombination would repeatedly cut up the blue chunks of DNA, shortening them by half each time, until after about four generations they would become indistinguishable from random noise. People with relatively recent ancestry tracing to two or more continents tend to have the most colorful paintings.

FIG. 4 is a diagram illustrating an embodiment of a display of ancestral data for an individual of African American descent. Display 400 indicates ancestral origins for an African American man. For example, display 400 may be displayed in response to a user selecting "African American Man" from menu 202. Also, display 400 may be displayed in response to a user selecting an icon corresponding to an African American (one of the icons in North America) in map 104.

Most African Americans have ancestry from both Europe and Africa. As a result, their ancestry paintings are mostly a mixture of navy and green (as shown), though the relative proportion of the two colors can vary widely.

There may be some small amount of noise present in the painting of a person's recent (the last 500 years or so) ancestry. In this example, there are a few brief stretches of orange (meaning Asian ancestry), as shown. The orange stretches are likely statistical noise rather than indicators of true Asian descent.

Legend 402 indicates that along each of the chromosomes, when the contributions of each region are summed, 64% of this African American's genome traces to European ancestors, 33% to Africans, and 4% Asians (which is likely noise). The gray intervals, such as the one at the left end of chromosome 13, are regions where the genotyping chip has no markers. These regions are not included in calculating the percentages.

Map 404 includes icons placed at various regions across the globe. The selected icon (highlighted in blue) is associated with an African American. Clicking on an icon causes the display to depict ancestral data for an example individual from the region where the icon is located.

Figure 5:
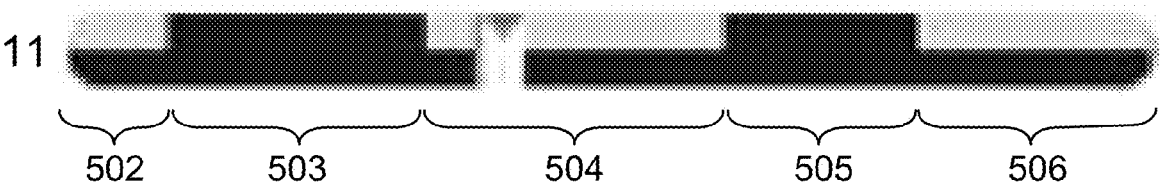
FIG. 5 is a diagram illustrating an embodiment of a display of ancestral data associated with a chromosome.

FIG. 5 is a diagram illustrating an embodiment of a display of ancestral data associated with a chromosome. Display 500 is an example display of ancestral data associated with chromosome 11. Display 500 includes five intervals across its length—intervals 502-506. Each interval is divided into an upper half and a bottom half. Each half represents a segment in a chromosome pair, where one segment is inherited from the mother and the other segment in the pair is inherited from the father of the individual. Each half is colored according to an ancestral origin associated with one parent. For example, in this case, two of them (intervals 503 and 505) are blue in both the top and bottom halves, meaning that this man inherited DNA tracing to European ancestors from both his mother and father. The other three intervals (intervals 502, 504, and 506) are each half blue and half green. That means in those locations, one copy of this man's DNA traces back to a European ancestor who lived in the last few hundred years, the other to an African ancestor. Thus, as depicted in this display, one interval along the graphical chromosome represents a pair of chromosome segments in a real chromosome.

In some embodiments, the ancestral data is unphased. In other words, it is not known which parent a particular segment of autosome came from. In any two-color interval, it is not indicated whether the top half or the bottom half was inherited from the mother or father. In some embodiments, when the ancestral data is unphased, the colors are ordered and the top half is colored with the color that is higher in order. For example, the order may be: Asia, Africa, Europe. In this case, orange will always be on top of green, which will always be on top of blue.

In some embodiments, the ancestral data is phased. Phased means that the individual's diploid genotype is resolved into two haplotypes, one for each chromosome. In other words, it is known from which parent a particular segment of autosome was inherited. For example, the top half may show the ancestral origins from the mother and the bottom half may show the ancestral origins from the father, or vice versa.

Figure 6:
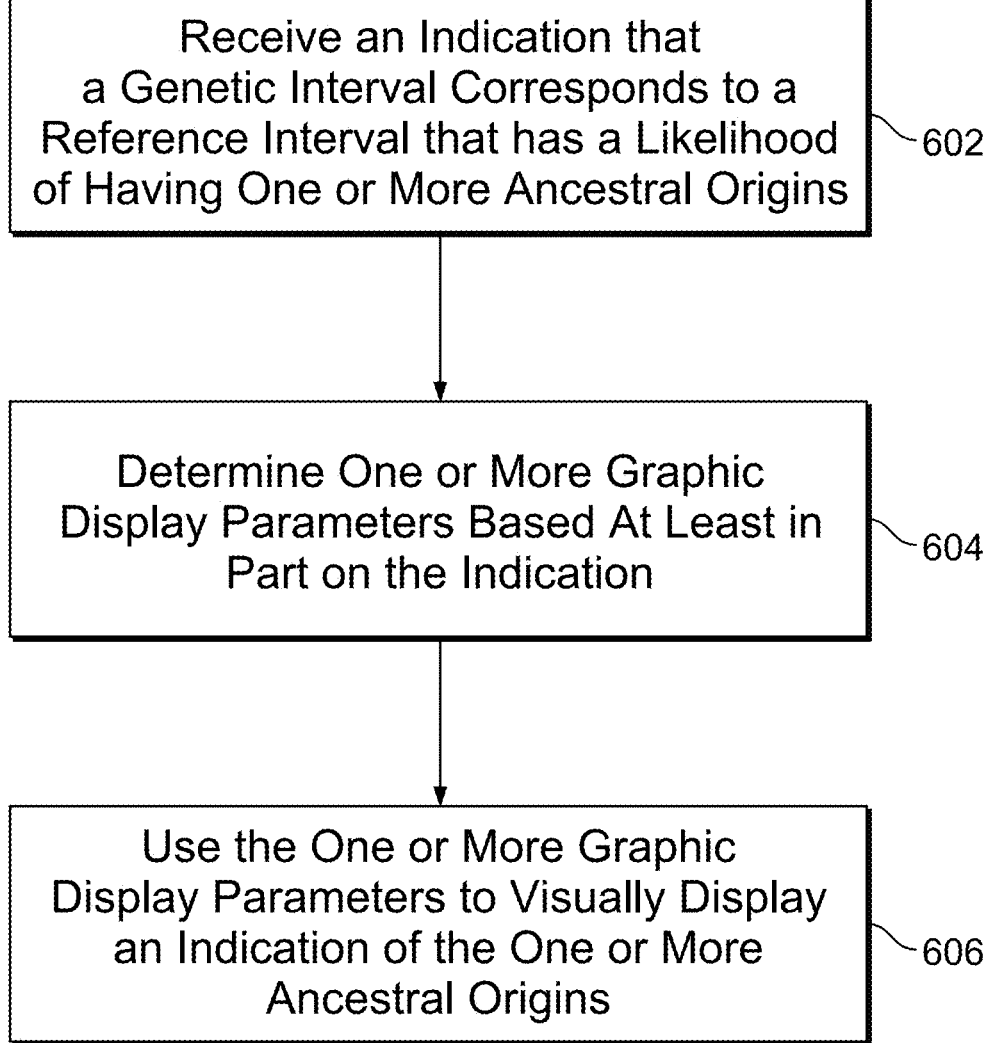
FIG. 6 is a flow chart illustrating an embodiment of a process for displaying ancestral data.

FIG. 6 is a flow chart illustrating an embodiment of a process for displaying ancestral data. For example, this process may be used to display any one of displays 100-500.

At 602, an indication that a genetic interval corresponds (e.g., matches) a reference interval that has a likelihood of having one or more ancestral origins is received. Depending on the embodiment, a genetic interval may include a chromosome segment (haploid) or a pair of chromosome segments (diploid). Thus, a genetic interval may be associated with one or two ancestral origins. A segment may include a sequence or set of SNPs along a chromosome. Examples of intervals include intervals 502-506. A reference interval is a genetic interval that has a likelihood of having one or more ancestral origins. For example, the likelihood may be determined based on a database of reference individuals who have known ancestral origins.

At 604, one or more graphic display parameters are determined based at least in part on the indication. Examples of the graphic display parameters include different colors (or visual patterns) that correspond to ancestral origins. For example, if the indication is that the genetic interval matches a reference interval that has a 90% likelihood of having African and Asian origin, then in some embodiments, it is determined that green and orange are graphical display parameters. In other embodiments, it might be determined that blue is a graphical display parameter, for example, based on the fact that neighboring intervals have a high likelihood of having European origin. In various embodiments, a variety of techniques may be used to obtain a graphic display parameter, as more fully described below.

At 606, one or more graphic display parameters are used to visually display an indication of the one or more ancestral origins. For example, if the graphical display parameters are blue and green, than an interval is painted blue and green, such as interval 502 in display 500.

Figure 7:
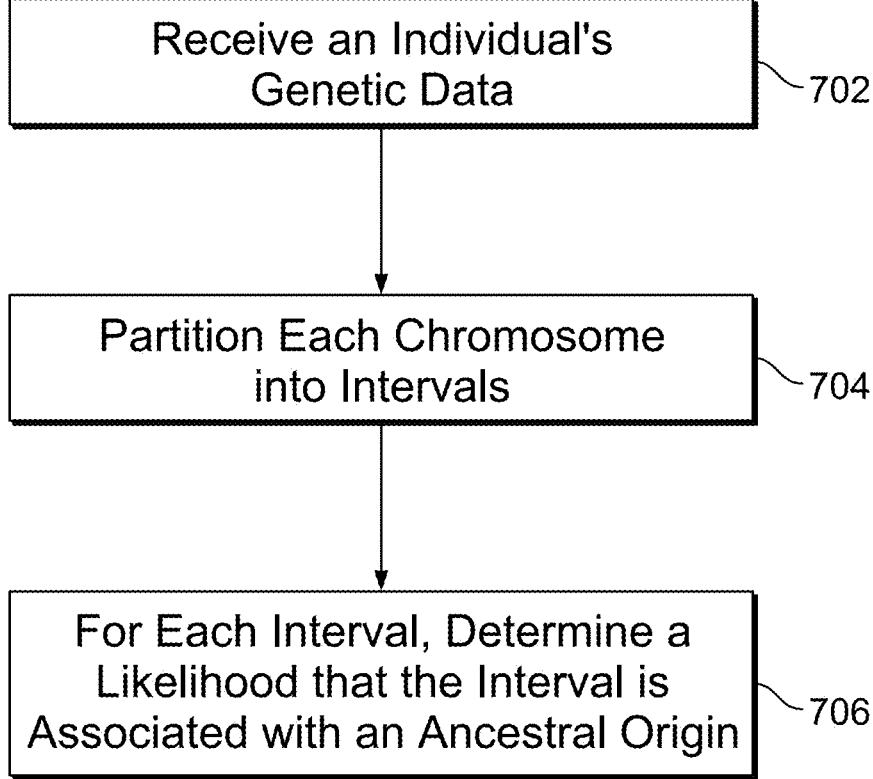
FIG. 7 is a flow chart illustrating an embodiment of a process for receiving an indication that a genetic interval matches a reference interval that has a likelihood of having one or more ancestral origins.

FIG. 7 is a flow chart illustrating an embodiment of a process for receiving an indication that a genetic interval matches a reference interval that has a likelihood of having one or more ancestral origins. For example, this process may be used to perform 602.

At 702, an individual's phased or unphased genetic data is received. For example, a genotyping chip, such as the Illumina HumanHap550v3 genotyping chip, may be used to assay an individual's genotype. As an example, genetic data for each of the non-gray segments shown in display 100 is obtained for an individual. The genetic data may be phased or unphased. If it is phased, then information regarding whether each location in a segment is inherited from the mother or the father of the individual is known. In some embodiments, phasing is performed using BEAGLE software, developed by Brian and Sharon Browning at the University of Auckland. Phasing can also be performed for an individual if the genetic data of one or both parents is known. Phasing refers to resolving an individual's diploid genotype into two haplotypes, one for each chromosome. In some embodiments, phased data includes data for one chromosome segment and an indication of a parent from which the data was inherited, and unphased data includes data for two corresponding chromosome segments in a pair of chromosome segments without an indication of a parent from which the data was inherited because this has not been determined. In the case of phased data, it is not necessarily known from which parent (mother or father) a phased chromosome segment comes from, in the absence of genetic data from the mother and/or father. What is known is that one phased segment came from one parent, and the homologous segment came from the other parent.

At 704, each chromosome is partitioned into intervals. In some embodiments, the intervals correspond to intervals in a table of genotype frequencies, as more fully described below. The interval may include diploid data or haploid data, depending on whether the data is phased or unphased. For example, in the case of phased data, each chromosome is partitioned into segments, e.g., of consecutive SNPs. In the case of unphased data, each chromosome pair is partitioned into segment pairs, e.g., of consecutive SNPs.

At 706, for each interval, likelihood that the interval is associated with an ancestral origin is determined. In the cased of phased data, a likelihood that the segment is associated with an ancestral origin is determined. In the case of unphased data, likelihood that the segment pair is associated with an ancestral origin is determined. In some embodiments, the likelihood is determined by looking up the interval in a table of genotype frequencies, as more fully described below.

Figure 8:
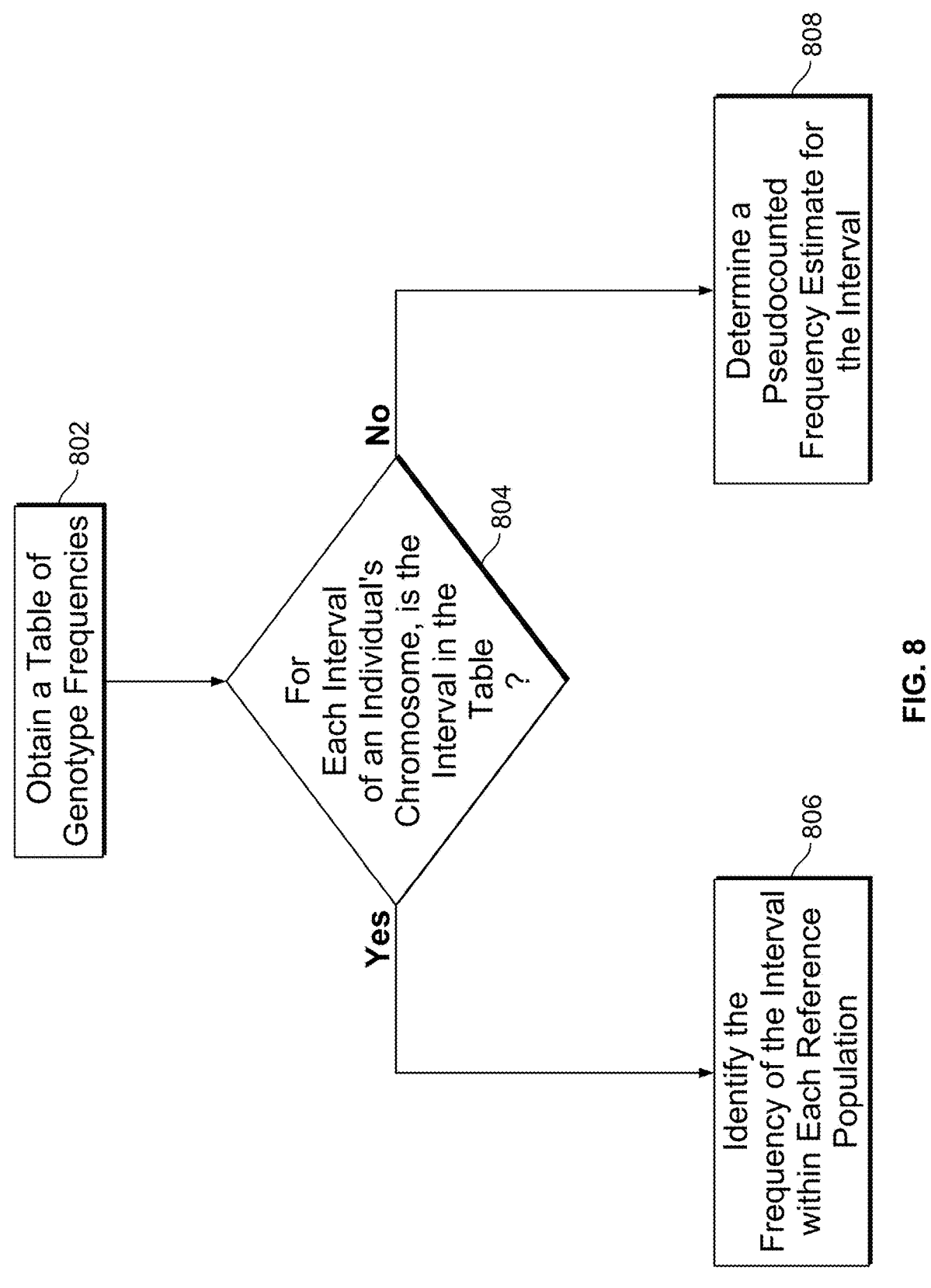
FIG. 8 is a flow chart illustrating an embodiment of a process for determining a likelihood that a genetic interval is associated with an ancestral origin.

FIG. 8 is a flow chart illustrating an embodiment of a process for determining likelihood that a genetic interval is associated with an ancestral origin. For example, this process may be used to perform 706. At 802, a database of genotype frequencies is obtained. In some embodiments, the database includes a table that maps a list of known genetic intervals to the corresponding frequencies of the genetic intervals within reference populations. In some embodiments, the table includes all possible genotypes of each interval within each reference population and the fraction of that population having that genotype. The fraction of a population having a genotype may also be referred to as the frequency or rate (of occurrence) of a genotype within a population. In the case of phased data, the reference populations include single ancestral origins to correspond to a segment of a single chromosome. In the case of unphased data, the reference populations include all combinations of two ancestral origins to correspond to a pair of segments from two chromosomes, as more fully described below.

At 804, for each interval of an individual's chromosome, an estimate of the frequency with which that interval is observed in the several reference populations is looked up in a table constructed for this purpose. The estimation method takes the reference population sample size into account, so that intervals not observed in the reference populations receive frequency estimates with small positive values instead of zero. In some embodiments, a pseudocounted frequency value of 0 is replaced with a small nonzero number because a frequency of 0 would be problematic in some implementations (e.g., implementations that include a division by 0). In some embodiments, at 808, the frequency is set equal to 0.

In some embodiments, 804 and 806 are repeated for all intervals until likelihood is determined for all intervals of the individual's genotyped data.

Figure 9:
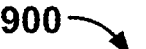
FIG. 9 is a flow chart illustrating an embodiment of a process for creating a table of genotype frequencies.

FIG. 9 is a flow chart illustrating an embodiment of a process for creating a table of genotype frequencies. For example, such a table may be obtained at 802. At 902, genetic data for a plurality of reference populations is received from one or more sources. For example, data may be obtained from sources such as the Centre d'Etude du Polymorphisme Humain (CEPH) Human Genodiversity Project or the International HapMap Project (www.hapmap.org).

In some embodiments, the data may be obtained from a database associated with a website that allows individuals to view and/or share with other users their genetic data. An example of such a website is www.23andme.com. Each user may provide data regarding their ancestral origin.

At 904, for each reference population, each chromosome of each reference individual is partitioned into intervals. In some embodiments, the intervals are nonoverlapping, adjacent words of consecutive SNPs, or points along the genome where individuals may differ. In some embodiments, the intervals overlap. In some embodiments, words of a fixed number of SNPs, such as ten SNPs are used. In some embodiments, words spanning a minimum genetic distance, e.g., 0.010 cM, as defined by the fine scale recombination map found at HapMap, are used with a threshold on the minimum number of SNPs per word.

If the data is unphased and reference populations of individuals of mixed ancestry are not available, then in some embodiments, at 906, a plurality of intervals corresponding to a synthetic reference population of synthetic individuals are generated from a population of real individuals, as more fully described below.

At 908, a rate of occurrence of each interval in each reference population is computed, which is also more fully described below.

FIG. 10A illustrates examples of genotype frequency tables. For example, these tables may be obtained at 802 and/or created by process 900. In this example, there are three reference populations: African (AFR), East Asian (ASN), and European (EUR).

Table 1000 is an example of a genotype frequency table for a particular interval j on a particular chromosome i, for the case of phased data. For the case of phased data, each interval is a segment. The possible values of the segment j on chromosome i in this example are: X, Y, and Z. For example, X may be ACAAGTACCTTGAAAAAATTT (SEQ ID NO: 1). In some embodiments, the genotype frequencies (i.e., 0.12, 0.42, 0.46, 0.02, 0.92, 0.06, 0.85, 0.04, and 0.11) are obtained according to 908 or as follows: For each reference population, for each value X, Y, and Z, the number of individuals in that reference population having that value at segment j, chromosome i, is determined.

The number of individuals is divided by the total number of individuals in that reference population to obtain the genotype frequency. For example, if there are 100 African individuals in the reference population and 12 of those individuals have genotype X at interval j on chromosome i, then the genotype frequency would be 12/100=0.12, as shown in table 1000. As shown, each column in table 1000 sums to 1.

Table 1004 is an example of a genotype frequency table for a particular interval j on a particular chromosome i, for the case of unphased data.

The data in table 1002 is discussed first. For the case of unphased data, each interval is a segment pair. In this example, the possible values of each segment are X, Y, and Z (as in table 1000). Therefore, the possible values of the segment pair j on chromosome i in this example are all possible combinations of X, Y, and Z: X/X, X/Y, Y/X, Y/Y, Y/Z, Z/X, Z/Y, and Z/Z. For example, X/X may be the pair ACAAGTACCTTGAAAAAATTT/ACAAGTACCTT-GAAAAAATTT. This is an example of generating a plurality of intervals corresponding to a synthetic reference population, or 906.

The possible reference populations are African/African, East Asian/East Asian, European/European, African/East Asian, African/European, and East Asian/European. The frequency of each segment pair value is determined by taking the product of the frequencies of the individual segments within a reference population. For example, the frequency of X in an African population (0.12) times the frequency of Y in an East Asian population (0.92) equals the frequency of X/Y in an African/East Asian synthetic population (0.1104). Because the data is unphased and there is no distinction between X/Y and Y/X, for each possible reference population, the frequency of X/Y and the frequency of Y/X can be summed under X/Y. For example, 0.1104 is summed with 0.0084 to produce 0.1188 for the above example. The same is true for X/Z and Z/X, and for Y/Z and Z/Y. This produces table 1004. This is an example of computing the rate of occurrence of each interval in each reference population, or 908.

For clarity, FIG. 10B illustrates how the values are obtained when going from table 1000 to table 1002. In this example, table 1006 shows table 1000 with variables B5-B7, C5-C7, and D5-D7 in each cell. Table 1008 shows how the frequencies from table 1006 are combined to produce the frequencies of the combinations shown in table 1002.

In some embodiments, the reference populations include individuals of mixed ancestry, and there is no need to generate synthetic reference populations. In this case, the genotype frequencies in table 1004 may be obtained as follows: For each reference population, for each possible value X/X, X/Y, X/Z, Y/Y, Y/Z, and Z/Z, the number of individuals in that reference population having that value at segment pair j, chromosome i, is determined. The number of individuals is divided by the total number of individuals in that reference population to obtain the genotype frequency. For example, if there are 1000 Asian/European individuals in the reference population and 17 of those individuals have genotype X/X at interval j on chromosome i, then the genotype frequency would be 17/1000=0.017, as shown in table 1004.

In some embodiments, some combination of synthetic and real reference populations is used to obtain the genotype frequencies in table 1004.

Tables 1000 and 1004 are examples of genotype frequency tables for a particular interval j on a particular chromosome i. In some embodiments, to display an indication of ancestral data for all 22 autosomes, there is a table for each interval on each chromosome. In some embodiments, as previously described, data is not available for all intervals since some genotyping chips do not have or have few markers in some segments. In various embodiments, data may be organized in a variety of ways. For example, the number of tables used may vary and/or other data structures besides tables may be used. In some embodiments, the data is implemented as a hash table for ease of lookup. Any appropriate type of lookup table may be used in various embodiments.

In addition, a variety of techniques may be used to obtain genotype frequencies. In various embodiments, any appropriate technique to obtain genotype frequencies may be used.

Figure 11:
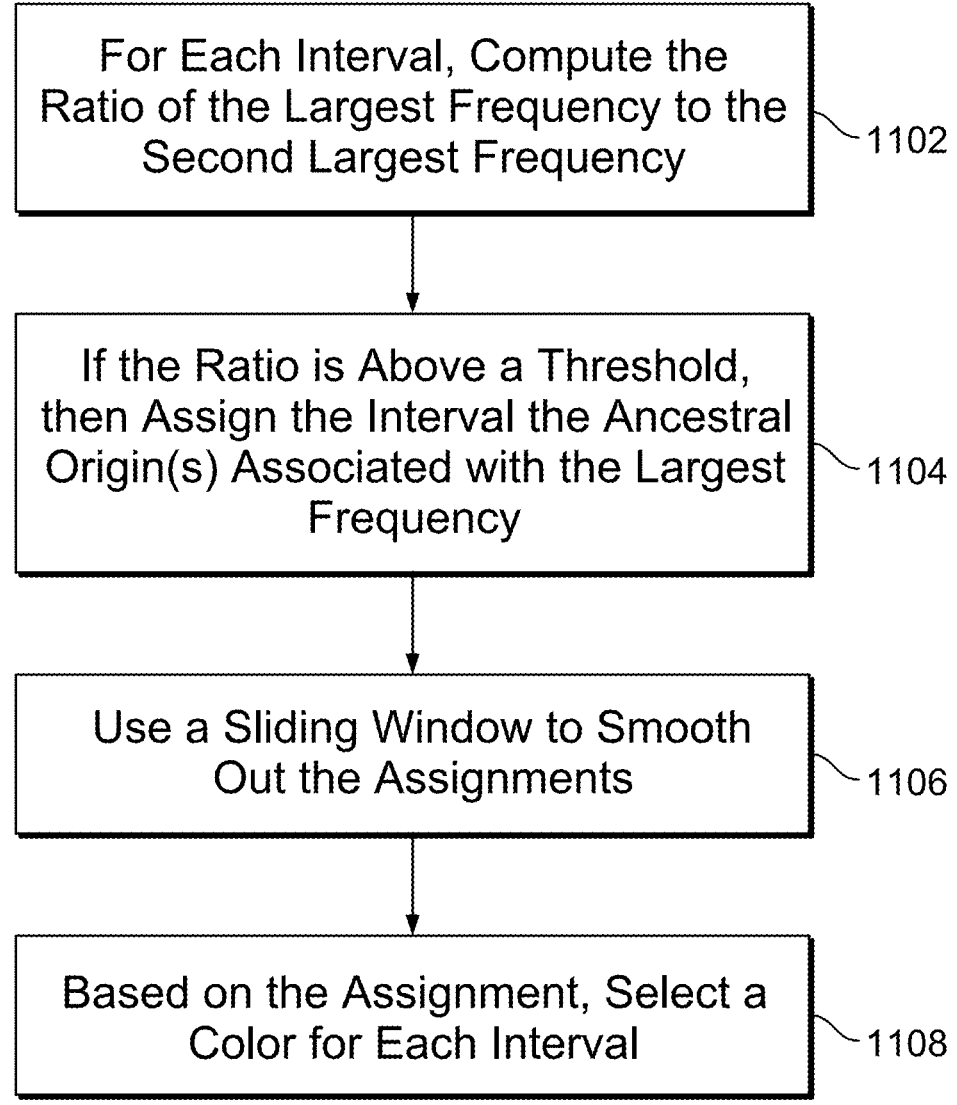
FIG. 11 is a flow chart illustrating an embodiment of a process for determining one or more graphic display parameters.

FIG. 11 is a flow chart illustrating an embodiment of a process for determining one or more graphic display parameters. For example, this process may be used to perform 604. At 1102, for each interval, the ratio of the largest frequency to the second largest frequency is computed. For example, a particular individual Greg has genotype X at interval j on chromosome i. (This is a phased example.) The frequencies associated with genotype X according to table 1000 are: AFR 0.12, ASN 0.02, and EUR 0.85. The ratio of the largest frequency to the second largest frequency is 0.85/0.12=7.08. At 1104, if the ratio is above a given threshold or above a given quantile, then the ancestral origin(s) associated with the largest frequency is assigned to the interval. In the above example, the ratio for Greg is 7.08. If the threshold is 5, then because 7.08>5, the ancestral origin of EUR is assigned to the interval j on chromosome i for Greg. If the threshold is 10, then the interval is unassigned. At 1106, a sliding window is used to fill in and/or smooth out the assignments. In various embodiments, this step is skipped or other types of smoothing or post processing are performed. As a result of the smoothing, an assignment of EUR may be changed to a different ancestral origin assignment, such as ASN. An example of how a sliding window fills in and/or smooths out assignments is more fully described below. At 1108, based on the final assignment, a graphic display parameter is selected for each interval. For example, a color is selected, where different colors correspond to different ancestral origins. In Greg's case, for interval j on chromosome i, if the assignment remains EUR after the processing of 1106, the color blue is selected for interval j on chromosome i. This is shown in display 100, where blue corresponds to European ancestral origin.

Figure 12:
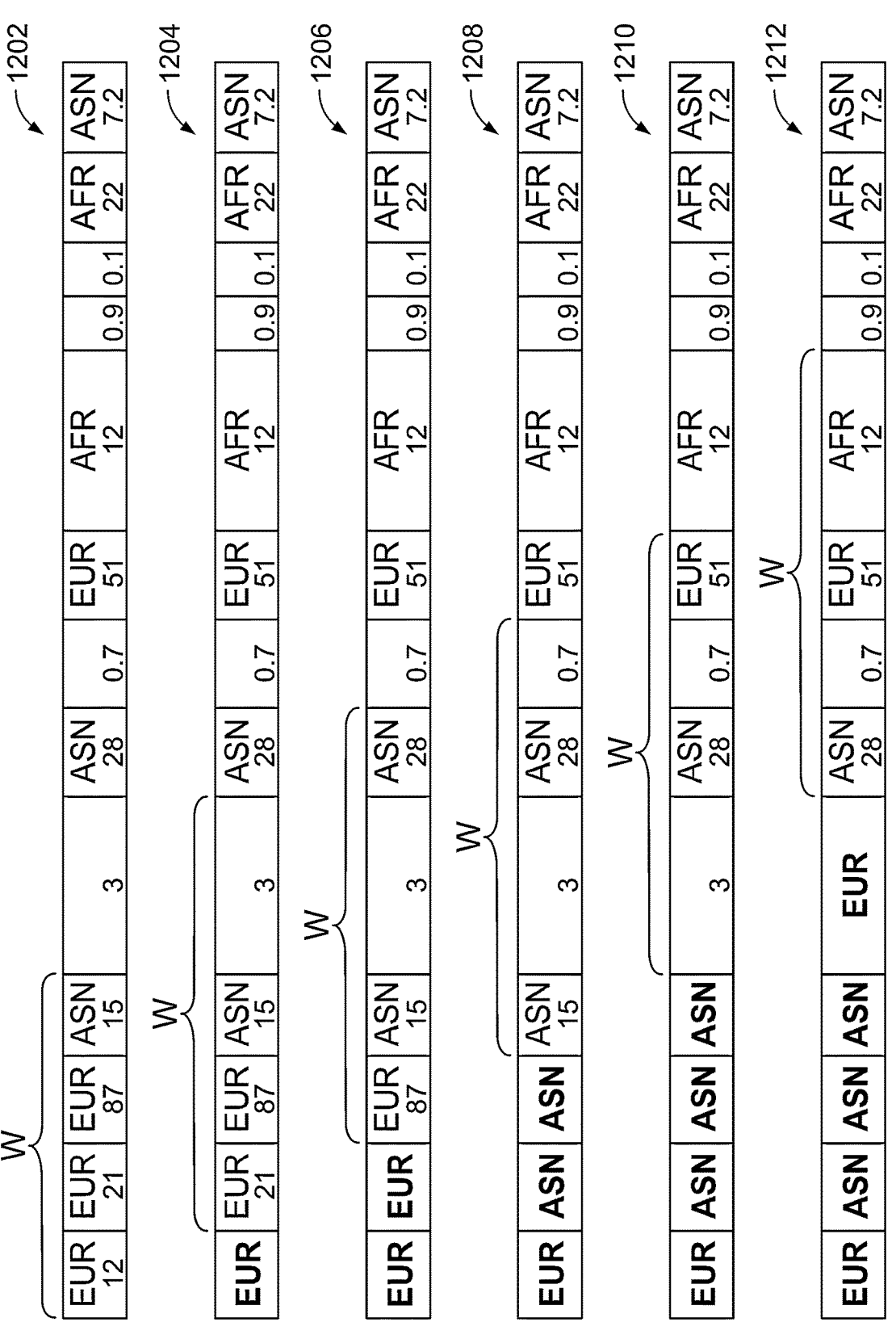
FIG. 12 is a diagram illustrating an embodiment of a sliding window used to smooth out ancestral origin assignments.

FIG. 12 is a diagram illustrating an embodiment of a sliding window used to smooth out ancestral origin assignments. In some embodiments, a dominant ancestral origin of a sliding window is estimated based on the segments in the sliding window, and that dominant ancestral origin is assigned to the first segment. The window slides by a segment, and the dominant ancestral origin of the segments in the sliding window is assigned to the second segment. In some embodiments, the dominant ancestral origin is estimated at least in part by determining the ancestral origin assigned to the majority of the segments in the sliding window.

Diagram 1202 illustrates consecutive segments of a chromosome, their assignments after 1104 and the ratio of the largest frequency to the second largest frequency for each. In this example, the threshold is 5. Therefore, if the ratio is below 5, an assignment was not made. A window of length W segments is used. In this example, W=4. In various embodiments W may be any appropriate length, such as 10-50. In some embodiments, the window length varies depending on the individual and/or chromosome. For example, if the assigned segments of a chromosome of an individual are all EUR, then the window length may be longer than if they are a mix of EUR and ASN. In diagram 1202, the window includes the first four segments with assignments EUR, EUR, EUR, and ASN. The majority is EUR, and so the first segment remains EUR, as shown in diagram 1204. In diagram 1204, the window has moved by one segment. The window now includes EUR, EUR, and ASN. The fifth segment does not count towards the vote because its ratio, 3, is below the threshold of 5. The majority is EUR, and so the second segment is still assigned EUR, as shown in diagram 1206. Similarly, at 1208, the third segment is assigned ASN. At 1210, the fourth segment is assigned ASN. At 1210, the window includes ASN and EUR, which is a tie. In some embodiments, the tie is broken by the segment with the higher ratio, in this case EUR with a ratio of 51, as shown at 1212. Ties may be broken in various ways in various embodiments.

In some embodiments, the window slides by more than one segment at a time. The distance by which a window slides each time is referred to as a slide length. A frame of segments is assigned the same ancestral origin at a time, where the frame has a length equal to the slide length. This may be the case because, depending on the display resolution, it may not be possible to display the ancestral origins at as fine a granularity as the segments. Therefore, it may be desirable to choose a slide length that is appropriate for the display resolution.

Other examples of post processing that may be performed at 1106 include sweeping for sharp discontinuities. For example, for each frame, if the neighboring frames have the same ancestral pair assignment, and it disagrees sharply with the ancestral-pair assignment of the frame, that frame is reverted to the ancestral-pair assignment of its neighbors. A sharp disagreement may be defined as one in which the intersection of the ancestral pairs is empty. This is seen in an example: frame 1 is African-European and frame 2 is Asian-Asian. Since frame 1 and frame 2 have no ancestry in common, i.e., their intersection is empty, the transition from frame 1 to frame 2 is sharp. If frame 1 were African-European and frame 2 were Asian-European, the intersection is "European", so the transition is not sharp.

Figure 13:
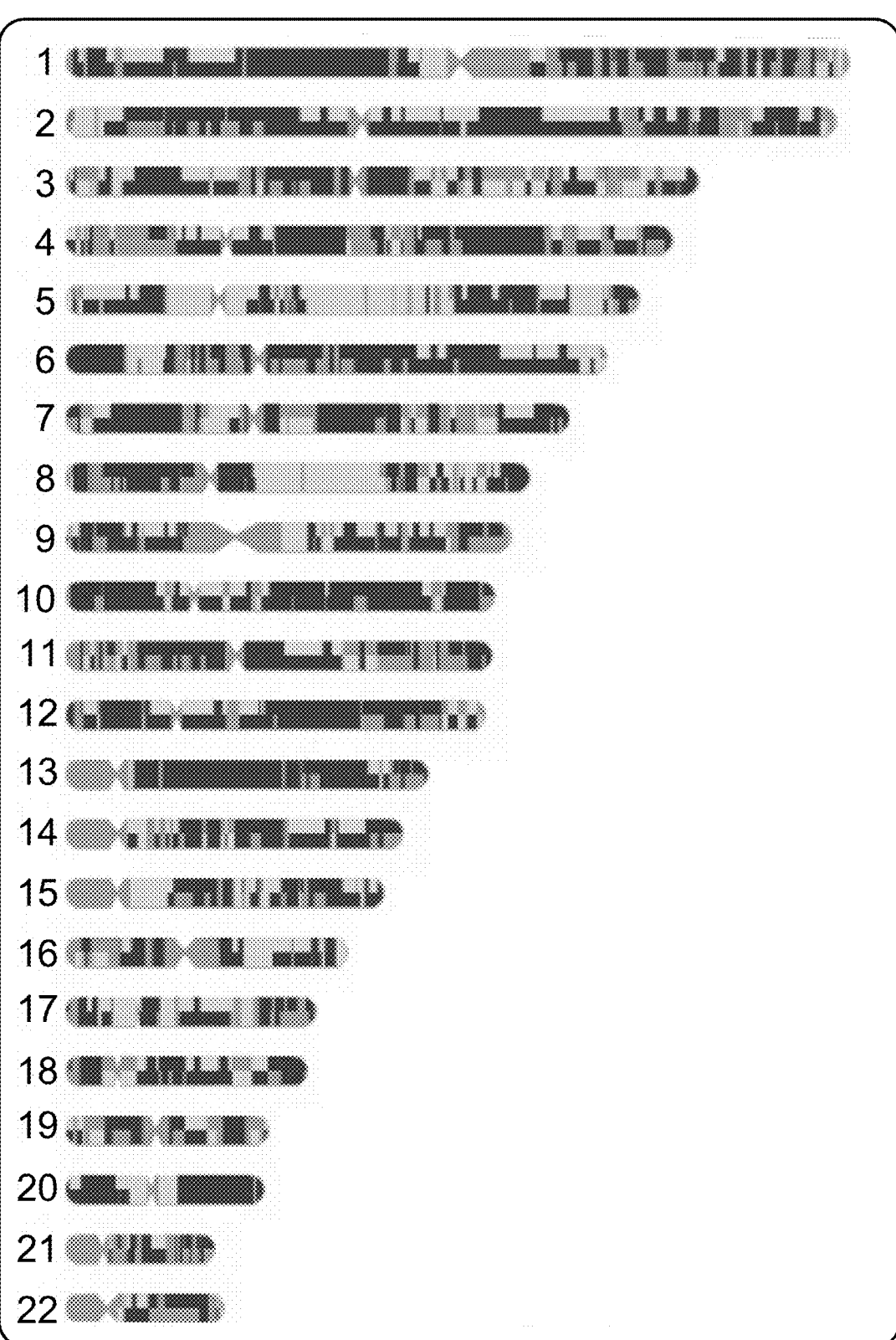
FIG. 13 is a diagram illustrating an embodiment of a karyotype view of a display of ancestral data for an individual.

FIG. 13 is a diagram illustrating an embodiment of a karyotype view of a display of ancestral data for an individual. This view shows the 22 autosomes. In some embodiments, the X chromosome is also shown. This view shows African, Asian, and European segments. In some embodiments, instead of dividing the individual's genome into African, Asian, and European segments, the karyotype view shows seven populations at the continental level. In some embodiments, the user can also choose to display the results corresponding to ancestral origins at the continental scale, regional scale (e.g., Northern Europe, East Africa, Western China), or subregional/local (e.g., a country, such as Ukraine or Ireland, or an ethnic group, such as Cherokee or Han). In some embodiments, by default, segments are displayed corresponding to the finest scale assignment that has been made. Display 1300 may also show and "paint" the user's Y chromosome (if male) and mitochondrial genome on the same display. As the Y and mitochondrion are each inherited as one indivisible unit of DNA sequence (without recombination), the painting procedure can match the DNA sequence to the ancestral origin where the DNA sequence is the most common.

Figure 14:
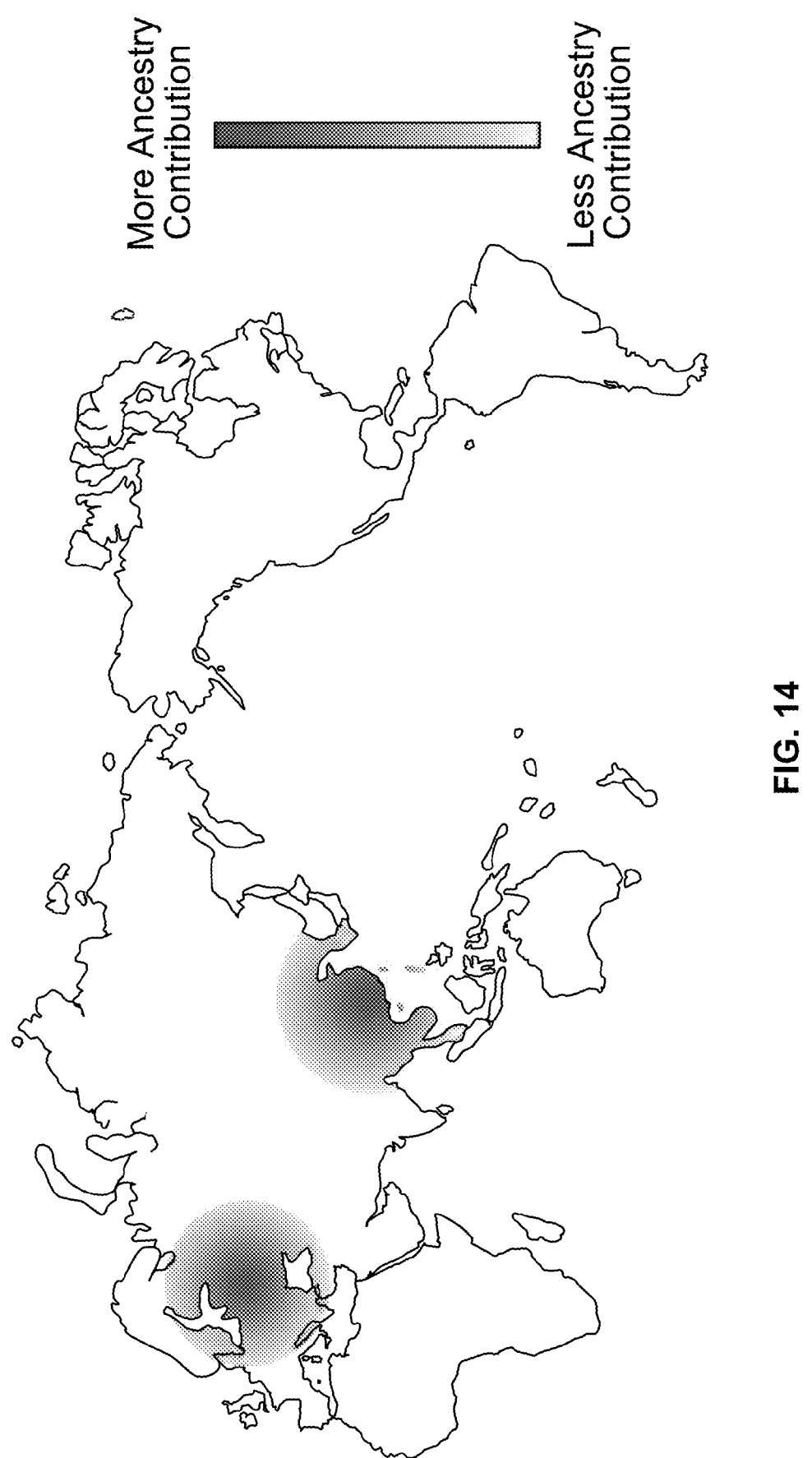
FIG. 14 is a diagram illustrating an embodiment of a personal landscape view of a display of ancestral data for an individual of Eastern European and East Asian ancestry.

FIG. 14 is a diagram illustrating an embodiment of a personal landscape view of a display of ancestral data for an individual of Eastern European and East Asian ancestry. This view uses the user's inferred ancestry to construct a spatial distribution showing where their ancestors are likely to have lived.

The blue discs on the world map indicate that this user has substantial ancestry deriving from Eastern Europe and East Asia. The intensity of the color encodes the proportion of the user's genome derived from that location on the Earth's surface. Alternatively, a contour plot or another density plot could be used. This painting would be expected for an individual having an Eastern European father and a Chinese mother.

Figure 15:
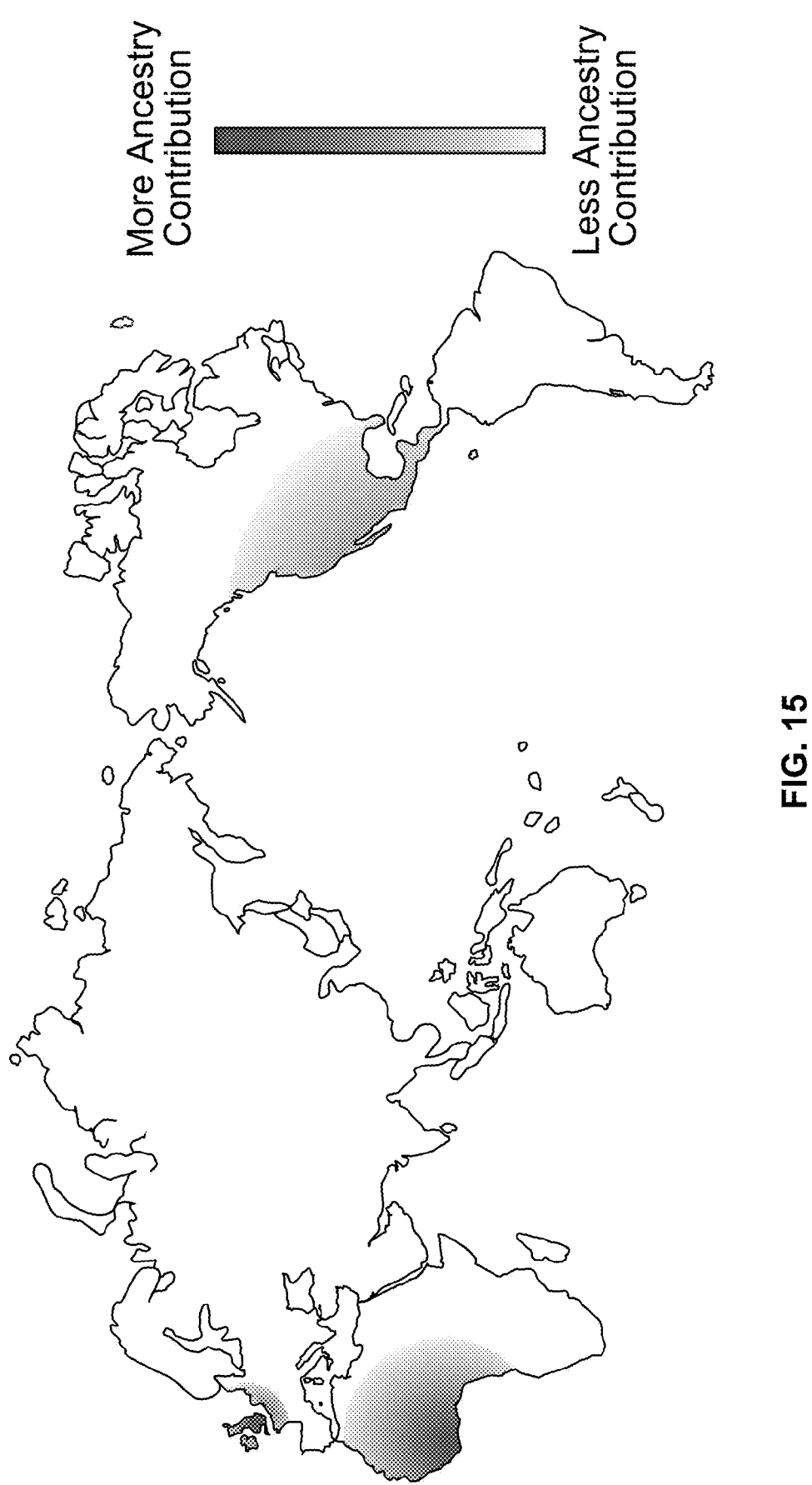
FIG. 15 is a diagram illustrating an embodiment of a personal landscape view of a display of ancestral data for an individual of African-American ancestry.

FIG. 15 is a diagram illustrating an embodiment of a personal landscape view of a display of ancestral data for an individual of African-American ancestry.

In this example, there are substantial contributions to the user's ancestry from West Africa, Northern Europe, and North America. Since the locations shown in the feature correspond to the locations of the world's people (just) prior to the era of intercontinental travel, this North American ancestry refers to Native American ancestry.

In some embodiments, the personal landscape view allows users to zoom in on their results. For users with wholly European ancestry or wholly East Asian ancestry, this allows them to see their results more readily.

In various embodiments, a user interface associated with any of the displays described herein provides controls to allow the user to interact with the data.

In some embodiments, users may also switch to a discrete representation of their results by toggling a "Mosaic" option. Rather than the smoothed landscapes depicted above, the user's ancestry is represented in terms of the world's national or regional boundaries. Countries colored more darkly contribute greater proportions of the user's ancestry.

In some embodiments, this view also allows the user to specify an arbitrary subset of the genome for visualization. Thus, if a user noticed an interesting stretch on Chromosome 6 in a karyotype view, they could look at the spatial distribution of ancestry from just Chromosome 6 in their personal landscape view.

Figure 16:
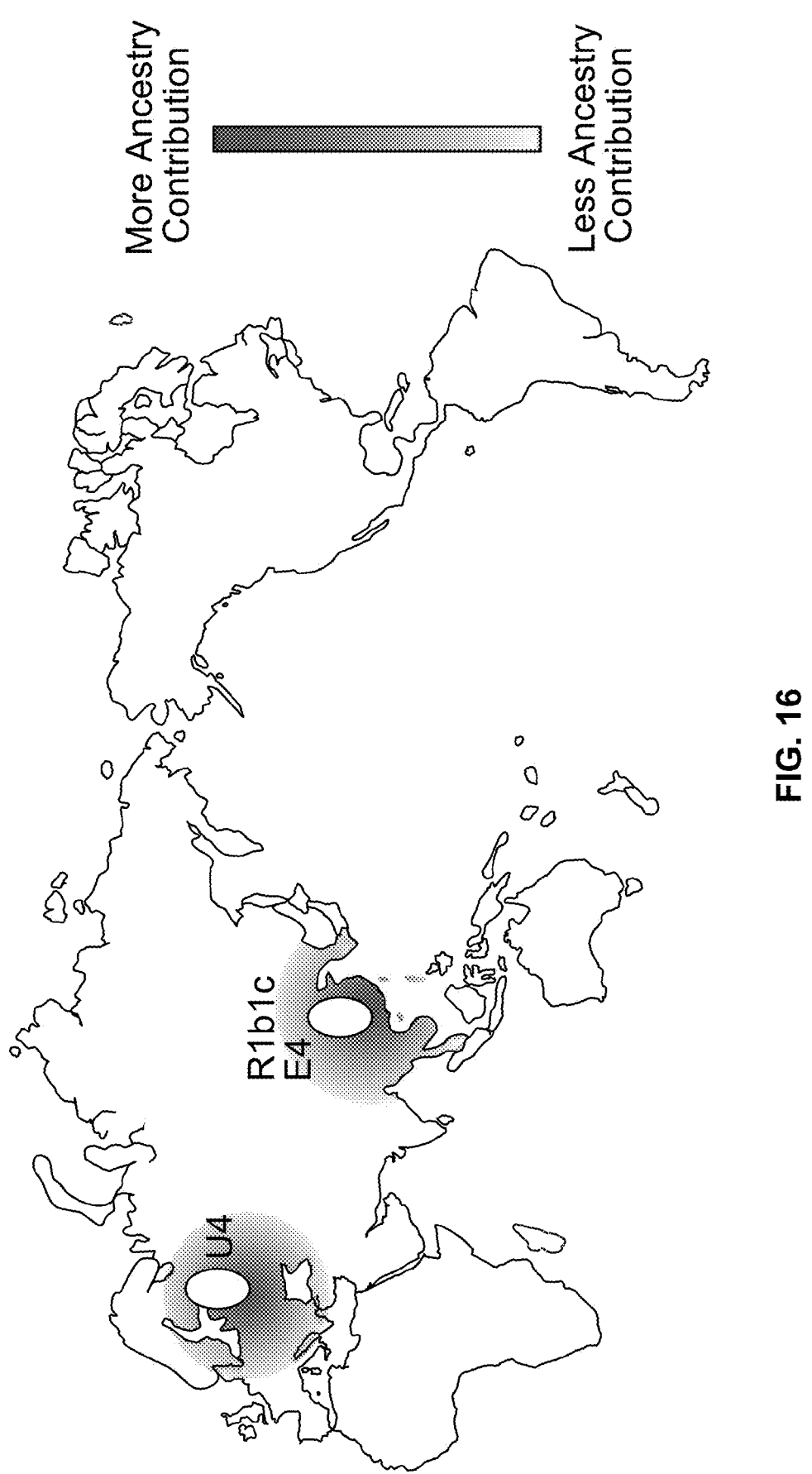
FIG. 16 is a diagram illustrating an embodiment of a personal landscape view of a display of ancestral data for an individual, in which markers are indicated.

FIG. 16 is a diagram illustrating an embodiment of a personal landscape view of a display of ancestral data for an individual, in which markers are indicated.

In some embodiments, markers can be added at the most likely geographic origins of the user's parents, grandparents, or more distant ancestors. Information can be included on each ancestor's Y and mitochondrial haplogroups, if this data is available. In this example, the user's father with Y haplogroup R1b1c, and mitochondrial haplogroup E4 is shown; the mother has mitochondrial haplogroup U4.

Figure 17:
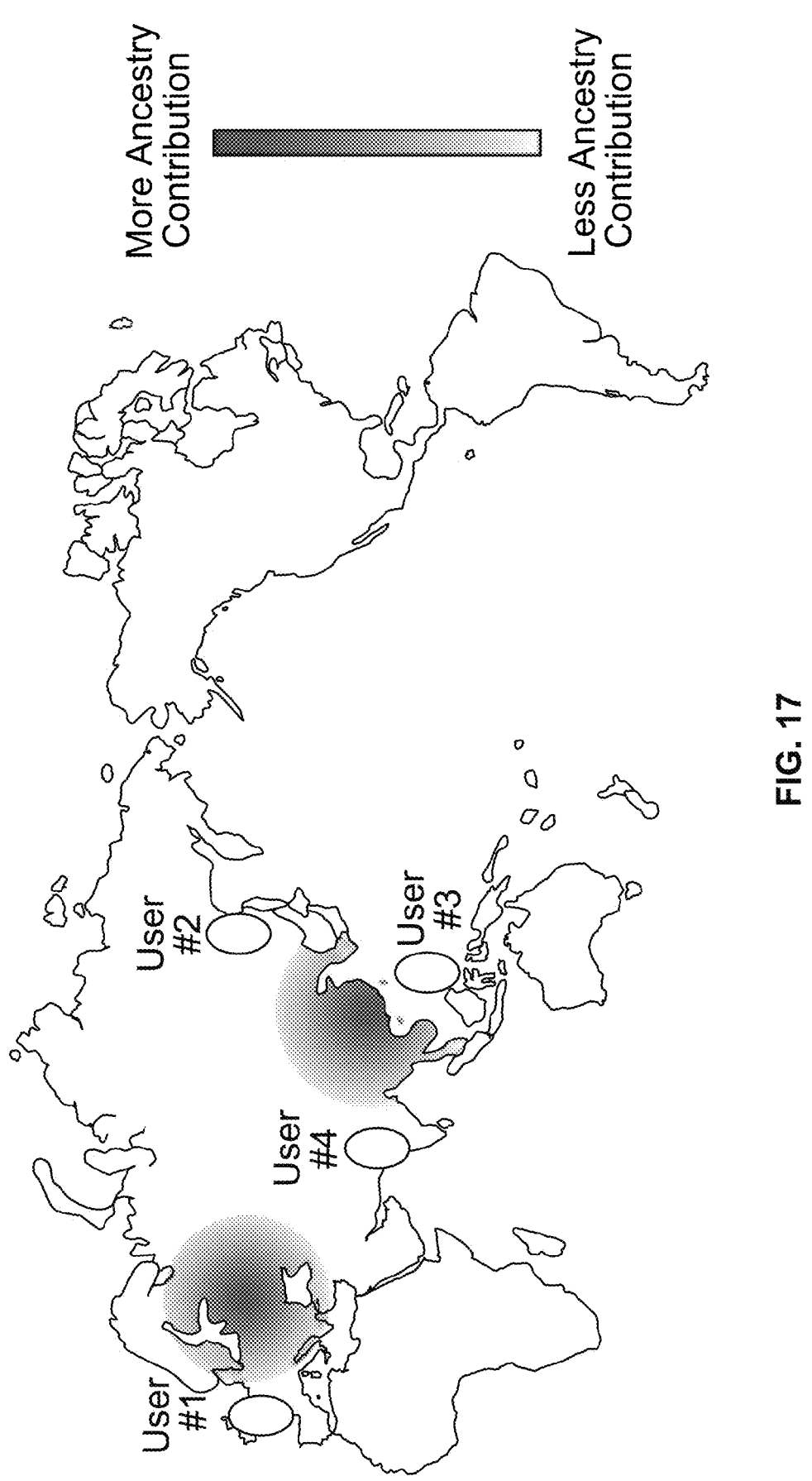
FIG. 17 is a diagram illustrating an embodiment of a personal landscape view of a display of ancestral data for an individual, in which multiple individuals are indicated.

FIG. 17 is a diagram illustrating an embodiment of a personal landscape view of a display of ancestral data for an individual, in which multiple individuals are indicated. Other individuals, such as the user's family and friends, are shown on the same map.

In some embodiments, the data may be obtained from a database associated with a website that allows individuals to view and/or share with other users their genetic data. An example of such a website is www.23andme.com. Within a database of genetic data, likely relatives can be determined by haplotype matching. In some cases, users can provide their ancestral origin; in other cases, ancestral origin can be computed using the techniques described above. These putative relatives can be displayed on the same personal landscape map. If the putative relatives appear in regions that concur with the user's own ancestry, this lends extra credence to these relationships.

Figure 18:
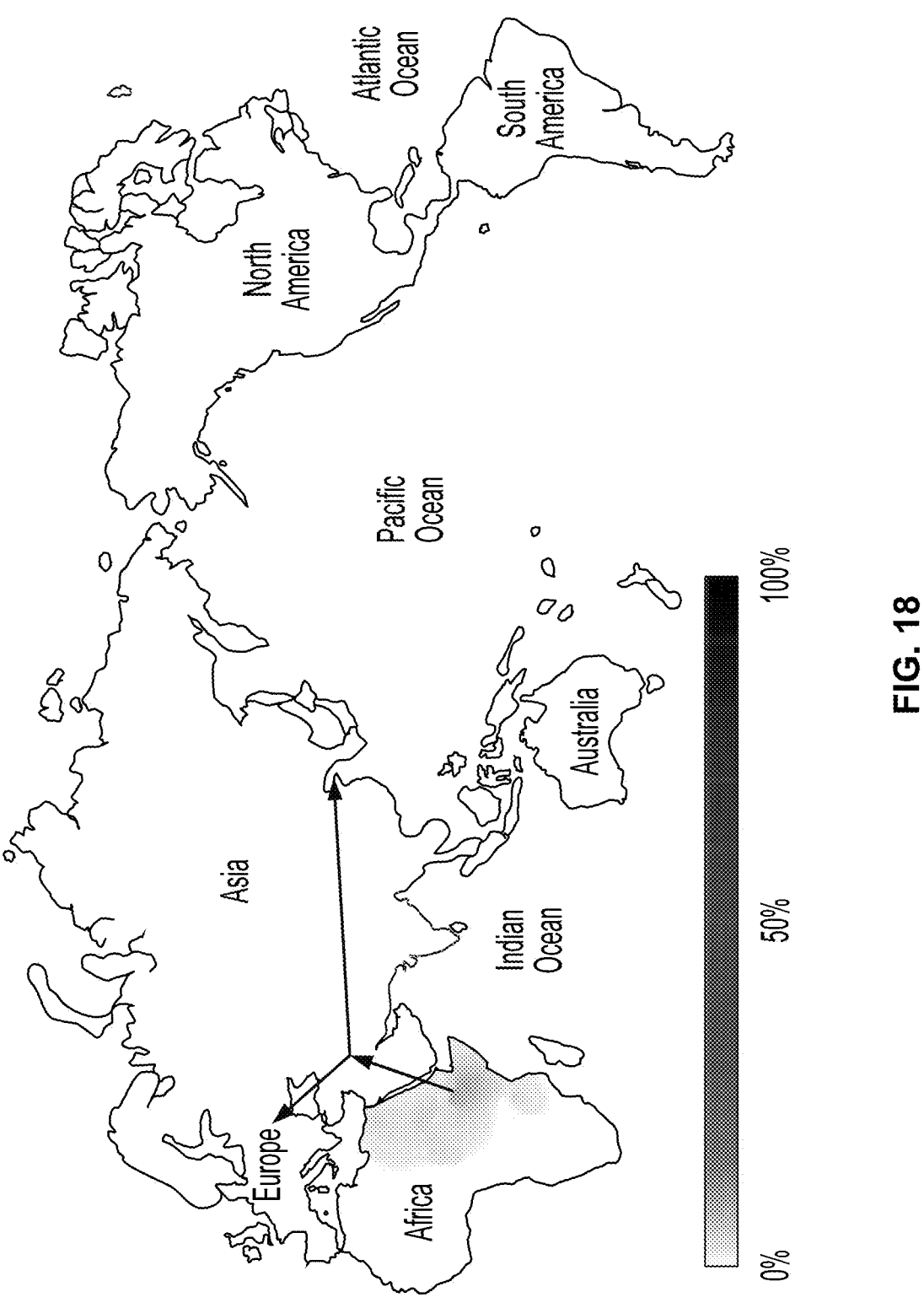
FIG. 18 is a diagram illustrating an embodiment of a personal landscape view of a display of ancestral data for an individual, in which migration information is indicated.

FIG. 18 is a diagram illustrating an embodiment of a personal landscape view of a display of ancestral data for an individual, in which migration information is indicated.

In this example, a migration of the user's ancestors is charted, by using known human migration patterns and the ultimate location of the user's haplotypes (before the era of intercontinental travel). For instance, in this example, the early migration out of Africa is shown, and from the techniques described above, it can be determined that the user's ancestors must have traveled to Asia and Europe, but not as far as the Americas.

FIG. 19 is a diagram illustrating an embodiment of a tabular view of a display of ancestral data for an individual. This view depicts a user's ancestral origins in a readily-grasped visual three column table. It derives loosely from the treemap visualization (e.g., explained under "Treemapping" of Wikipedia).

The three divisions in the table correspond to the three levels of hierarchy in the data set: continental, regional, and local. This is a tabular view representation that might correspond to the half-European/half-Asian individual discussed above. Each of the columns in the table divide the user's ancestry into proportions (that add up to 100%). The gray-colored regions correspond to unassigned regions of the user's genome, due to noninformative markers or due to lack of data. The columns provide increased spatial resolution of assignment as they proceed to the right, and the unassignable proportion also tends to increase. Thus the assignable portion of this user's genome can be seen to be about 50/50 European/East Asian in the leftmost column. All of the European ancestry that is assignable at the regional level comes from Eastern European populations, and at the local level can be seen to be derived from Ukrainian and Russian ancestors. All of the East Asian ancestry that is assignable at the regional level comes from Eastern Chinese populations, and at the local level can be seen to be derived from Han ancestors.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A computer-implemented method comprising:
partitioning genetic data into intervals;
determining, based on the genetic data and frequencies of genotypes appearing in the intervals for each of a set of reference populations, geographic origins for one or more of the intervals;
generating, for display on a graphical user interface, representations of the intervals indicating the geographic origins for the one or more of the intervals; and
providing, to the graphical user interface, the representations of the intervals.

2. The computer-implemented method of claim 1, further comprising:
determining, based on the genetic data and the frequencies of genotypes appearing in the intervals for each of the set of reference populations, one or more further intervals with no known geographic origins, wherein the representations of the intervals indicate that there are no known geographic origins for the one or more further intervals.

3. The computer-implemented method of claim 1, wherein the intervals are based on non-overlapping adjacent words of consecutive single-nucleotide polymorphisms.

4. The computer-implemented method of claim 1, wherein the intervals are based on fixed-sized words of consecutive single-nucleotide polymorphisms.

5. The computer-implemented method of claim 1, wherein the geographic origins include at least Europe, Asia, and Africa.

6. The computer-implemented method of claim 1, wherein the graphical user interface includes a drop-down menu that lists a plurality of individuals, and wherein selection by way of the drop-down menu causes the graphical user interface to display the representations of the intervals.

7. The computer-implemented method of claim 1, wherein the graphical user interface includes a geographic map of the geographic origins for the one or more of the intervals.

8. The computer-implemented method of claim 1, wherein the graphical user interface includes a geographic map, and wherein the geographic map includes a spatial distribution of the geographic origins.

9. The computer-implemented method of claim 1, wherein the graphical user interface includes a geographic map, and wherein the geographic map includes indications of the geographic origins for a Y haplogroup or a mitochondrial haplogroup.

10. The computer-implemented method of claim 1, wherein the graphical user interface includes a geographic map, and wherein the geographic map includes indications of migration patterns for ancestors of an individual with the genetic data, wherein the migration patterns are based on known human migration patterns and a geographic location of a haplotype of the individual.

11. The computer-implemented method of claim 1, wherein the intervals are arranged in the graphical user interface in a karyotype view including 22 autosomal chromosomes.

12. The computer-implemented method of claim 11, wherein the intervals of the 22 autosomal chromosomes are represented as pairs, and wherein the geographic origins for the intervals within each pair are separately indicated.

13. The computer-implemented method of claim 1, wherein the geographic origins are each represented by different colors.

14. The computer-implemented method of claim 1, further comprising:

determining the frequencies of genotypes appearing in the intervals for each of the set of reference populations by, for each respective interval of the intervals:

determining a first number of individuals within each respective reference population of the reference populations exhibiting a respective genotype; and dividing the first number by a second number representing a total of the individuals within the reference populations.

15. The computer-implemented method of claim 1, wherein the frequencies of genotypes appearing in the intervals for each of the set of reference populations include at least one synthetic rate of genotype occurrence for a synthetic reference population of mixed geographic origins.

16. The computer-implemented method of claim 1, wherein determining the geographic origins for the one or more of the intervals comprises:

determining, for a specific interval of the one or more of the intervals, a ratio of a largest frequency of genotype occurrence to a second largest frequency of genotype occurrence within the specific interval;

determining that the ratio is above a given threshold or a given quantile; and based on the ratio being above the given threshold or the given quantile, assigning, to the specific interval, a geographic origin for a genotype associated with the largest frequency of genotype occurrence.

17. The computer-implemented method of claim 1, wherein determining the geographic origins for one or more of the intervals comprises:

arranging, for a specific interval of the one or more of the intervals, a window of n consecutive intervals including the specific interval; and assigning, to the specific interval, a majority geographic origin of the n consecutive intervals within the window.

18. The computer-implemented method of claim 17, wherein n is a value from 10 to 50.

19. A non-transitory computer-readable medium storing program instructions that, when executed by one or more processors of a computing system, cause the computing system to perform operations comprising:

partitioning genetic data of an individual into intervals;

determining, based on the genetic data and frequencies of genotypes appearing in the intervals for each of a set of reference populations, geographic origins for one or more of the intervals;

generating, for display on a graphical user interface, representations of the intervals indicating the geographic origins for the one or more of the intervals; and providing, to the graphical user interface, the representations of the intervals.

20. A computing system comprising:

one or more processors;

memory; and program instructions, stored in the memory, that upon execution by the one or more processors cause the computing system to perform operations comprising:

partitioning genetic data into intervals;

determining, based on the genetic data and frequencies of genotypes appearing in the intervals for each of a set of reference populations, geographic origins for one or more of the intervals;

generating, for display on a graphical user interface, representations of the intervals indicating the geographic origins for the one or more of the intervals; and providing, to the graphical user interface, the representations of the intervals.

\* \* \* \* \*